United States Patent [19]

Inoue

[11] Patent Number: 4,589,848

[45] Date of Patent: May 20, 1986

[54] TONGUE PRESS

[75] Inventor: Miyako Inoue, Tokyo, Japan

[73] Assignee: Inoue Attachment Co., Ltd., Tokyo, Japan

[21] Appl. No.: 699,351

[22] Filed: Feb. 7, 1985

[51] Int. Cl.[4] ............................................... A61C 5/00
[52] U.S. Cl. ....................................... 433/140; 128/15; 433/93
[58] Field of Search ................... 433/38, 140, 146, 93; 128/12, 13, 14, 15, 16

[56] References Cited

U.S. PATENT DOCUMENTS 2,634,500  4/1953  McAdoo ............................... 433/39
2,680,295  6/1954  Craigo ................................. 433/140

Primary Examiner—Robert Peshock
Attorney, Agent, or Firm—Roy F. Hollander

[57] ABSTRACT

This invention provides a tongue press that can be switchably adapted to both external and internal tongue press holder. The tongue press can be embodied in various types such as the type covering the whole surface area of the tongue and the type covering one half or one side of the tongue and is also featured by a reticulate structure so as to alleviate the malaise of the patient applied with the device while eliminating slip of the tongue due to saliva, etc., in use of the device. The invention allows the selective use of any desired type of tongue press according to the patient and the purpose of use. Owing to the flexiblity provided by the reticulate structure, a single tongue press according to this invention can be used for many patients differing in size and shape of the tongue. Also, the production cost of the tongue press can be reduced.

6 Claims, 18 Drawing Figures

TONGUE PRESS

BACKGROUND OF THE INVENTION

1. Field of the Invention

This invention relates to an ancillary device for dental treatments, and more particularly to a tongue press adapted to a tongue press holder and used for holding in position and protecting the patient's tongue in a dental treatment of the inside of a tooth or teeth on the mandible so that the patient's tongue won't be injured by a treating instrument even when the patient's tongue is moved inadvertently or the dentist's fingers slip or are improperly handled in the patient's month during the treatment.

2. Description of the Prior Art

In dental treatments, high-speed cutting and polishing tools are often used for chipping out or abrading the affected part of a carious tooth.

An important problem in such dental treatments, especially in the treatment of the inside of a tooth or teeth on the mandible, is how to protect the patient's tongue, which is sensible and has a great many of blood vessels therein, from the treating instruments such as cutting and polishing tools.

In fact, it is not rare in the dental treatments that the patient's tongue be injured by a treating instrument which happen to touch the patient's tongue as a result of an inadvertent movement of the tongue or slip of the dentist's fingers in the mouth.

As the protective devices of the type under consideration, there have been proposed an external tongue holder (Japanese Patent Application No. 18936/83) which is adapted externally to the mandible of a patient for fixing his tongue in position in the mouth while covering the upper side of the tongue so as to securely protect the patient's tongue during the treatment, and an internal tongue holder (Japanese Utility Model Application Nos. 153236/82 and 153237/82) similar in principle to said external type but applied interiorly in the oral cavity. These applications have been filed by the same applicant as the present application in Japan.

Referring to the accompanying drawings, FIG. 13 is a perspective view of said external tongue holder adapted with a known type of tongue press, and FIG. 14 is a diagrammatic side view of the mandible of a patient to which the external tongue holder of FIG. 13 has been applied. In these drawings, reference numeral 4 designates the external tongue press holder, 5 a joining member and 6 a lower jaw supporting member.

Said external tongue press holder 4 consists of a tongue press 7 having a central body portion 18 and an integral edge portion 19 designed to cover and hold in position the top, front and both side sections of the tongue 2 at a location near the inner periphery of the lower gingiva 3, said central body portion 18 having a joining protuberance 20 centrally on its upper side; a lower jaw supporting member 6 having a jaw sustaining portion 14 configured in conformity to the contour of the lower jaw 1 and positioned in opposition to said tongue press 7 so as to help to fix the tongue in position in the mouth, a rising portion 15 which rises up substantially vertically from an end of said jaw sustaining portion 14, and a joining portion 17 cranked substantially at right angles from the upper end of said rising portion 15 so that said joining portion 17 is substantially parallel to said jaw sustaining portion 14, said joining portion 17 being formed centrally thereof with a connecting hole 16; and a connecting member 5 having a joining portion 10 formed with holes 9 into one of which is securely fitted the protuberance 20 of said tongue press 7, a curved portion 11 extending from an end of said joining portion 10 with a proper curvature so as to bypass the lower gingiva 3, and a vertical portion 12 extending down vertically from said curved portion 11 (substantially vertically to said joining portion 10), passed through the connecting hole 16 of said supporting member 6 and provided with a stopper 13 at the lower end thereof.

In use of this external tongue press holder 4, first the jaw supporting member 6 is lowered down sufficiently to provide an ample spacing between said tongue press 7 and the jaw sustaining portion 14 of said supporting member 6 and then the tongue press 7 joined integral to the connecting member 5 is placed into the mouth so as to cover and hold down the tongue 2 in position. Then the supporting member 6 is pushed upward, with the hole 16 in said supporting member 5 being kept perpendicular to the vertical portion 12 of the connecting member 5, until the jaw sustaining portion 14 is brought into tight attachment against the jaw. Under this condition, the operator lets go his hold on the device, whereby the joining portion 17 is frictionally secured to the connecting member 5 with a slight slant to the vertical portion 12 of said connecting member 5.

FIG. 15 is a perspective view of a conventional internal tongue press holder, and FIG. 16 is a diagrammatic side view of the mouth of a patient where said internal tongue press holder was properly set in its use position. In the drawings, numeral 21 designates the conventional internal tongue press holder, 22 a tongue press, and 23 an elastic curved portion of the holder.

This internal tongue press holder 21 consists of a tongue press 22 adapted to cover the upper part of the tongue 2 and hold it in position near the inner periphery of the lower gingiva 3 and an elastic curved portion 23 joined at its lower end to said tongue press 22, curved elastically at its middle part toward the pharynx of the patient and having at its upper end a tooth abutment 24 which is attached to the ends of the foreteeth 25.

In use of this internal tongue press holder 22, the patient is asked to open his mouth and the operator inserts the tongue press holder 21 into the patient's mouth while slightly flexing the elastic curved portion 23, placing the tongue press 22 just inside of the lower gingiva 3 so that said tongue press 22 covers the upper part, front part and both sides of the tongue to hold it in position near the inner periphery of the lower gingiva 3. The elastic curved portion 23 is curved toward the pharynx of the patient and the tooth abutment 24 at the upper end thereof is engaged with the foreteeth so that the flexing force of said elastic curved portion 23 is exerted to the press holder 22 to let it hold down the tongue 2 securely in position.

Said both external and internal tongue press holder 4 and 21 were generally satisfactory in protecting the patient's tongue from the treating instruments in the dental treatments, but the tongue press 7, 22 had the problems such as unpleasant feeling of the patient in application of the device, production cost, etc.

FIG. 17 is a top plan view of a conventional tongue press 7, and FIG. 18 is a sectional view taken along the line D—D of FIG. 17.

The conventional tongue press 7 is made of a natural or synthetic rubber material and produced by injection molding or other like means to have a configuration conforming to the tongue shape so as to cover the upper, front and both side parts of the tongue excepting the basal part thereof as illustrated in FIG. 17. On the upper side 18 of said tongue press is provided a protuberance 20 which is to be fitted into a fixing hole 9 formed in the external tongue press holder 4.

Also, as illustrated in FIG. 18, the central body portion 18 and the edge portion 19 of said tongue press 7 differ in thickness so that the upper edge portion 19 has a flexibility to accommodate the individual differences in tongue size and shape.

However, the man's tongue size and shape differ greatly depending on not only age and sex but also individually and only one tongue press can not entirely accommodate such differences in tongue size and shape, so that it was necessary to prepare the tongue presses of various sizes and shapes.

Further, since the conventional tongue press 7 or 22 was flat and smooth at its surface contacting the patient's tongue 2, patient's saliva tended to get in between the tongue 2 and tongue press 7, 22 to give an unpleasant clammy sense to the patient, and also the tongue press 7, 22 would slip on the tongue 2, making it unable to securely hold the tongue 2 in position.

Moreover, the mold for producing a tongue press 7 differing in thickness at its central body portion 18 and edge portion 19 as illustrated in FIG. 18 must be varied in clearance between the cope and drag at its sections corresponding to said central body portion 18 and edge portion 19 of the tongue press, and this, coupled with the necessity of forming the intricate carvatures conforming to the individual tongue size and shape, has made the production of the mold very costly.

SUMMARY OF THE INVENTION

The present invention is to provide a tongue press that can be switchably adapted to both external and internal tongue press holders, said tongue press having a reticulate structure so as to alleviate the patient's malaise in use of the device while eliminating slip of the tongue due to saliva and to also provide the tongue press with a large flexibility to accommodate all the varieties of tongue size and shape. Further, it is unnecessitated according to this invention to vary the thickness of the central body portion of the tongue press from that of the edge portion, so that the cost for the mold is reduced to allow production of the tongue press at low cost.

Moreover, according to the reticulate tongue press of this invention, even if saliva gets in between the tongue press and tongue, such saliva can flow out of the tongue press and therefore doesn't cause slip of the tongue press on the tongue.

The present invention also provides a tongue press designed to protect only one side of the patient's tongue to further improve the sense of use to the patient while facilitating the dentist's treatment.

DETAILED DESCRIPTION OF THE PREFERRED EMBODIMENTS

Figure 1:
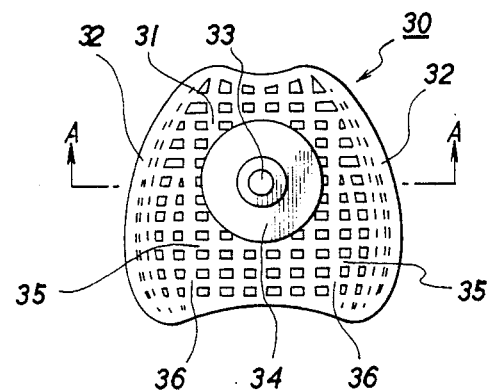
FIG. 1 is a top plan view of a whole-covering type tongue press according to an embodiment of this invention.
Figure 2:
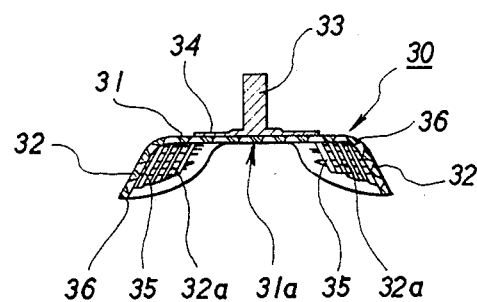
FIG. 2 is a sectional view taken along the line A—A of FIG. 1.

FIG. 1 is a top plan view of a whole-covering type tongue press according to a first embodiment of this invention, and FIG. 2 is a sectional view taken along the line A—A of FIG. 1. In these drawings, reference numeral 30 designates generally the whole-covering type tongue press, 31 the central body portion thereof, and 32 the edge portion thereof.

This whole-covering type tongue press 30 has a configuration conforming generally to the countour of the tongue so as to cover the substantially whole part of the tongue excepting its basal part and tip. The tongue press 30 has a reticulate structure constituted by lateral strips 35 and vertical strips 36.

Substantially centrally of the upper side of the central body portion 31 of said tongue press 30 are provided a disc-shaped force-dispersing fitment 34 adapted for dispersing throughout the structure the pressing force exerted to the tongue press 30 and a lobe-like protuberance 33.

The edge portion 32 of the tongue press is formed integral with said central body portion 31 and designed to cover and hold both side edges of the patient's tongue in position while protecting the tongue from being injured by a treating instrument.

It will be seen that the tongue press is cut out at its portion corresponding to the tongue tip. This is intended to keep the tip portion of the patient's tongue open to the ambient for diminishing the sense of compression to the patient's tongue and to give a flexibility to the tongue press 30. (The contact areas 31a and 32a of the central body portion 31 and edge portion 32 with the tongue are so constructed that the lateral strips 35 are greater in thickness than the vertical strips 36 as shown in FIG. 2 so that the lateral strips 35 alone will touch the patient's tongue in use of the device. This is intended to improve the feeling of the patient in application of the device to the patient's tongue). The thickness, number and direction of said both lateral and vertical strips 35 and 36 can be suitably selected to offer the best adaptability of the device to the patient's tongue.

The lateral strips 35 are formed with a uniform thickness throughout both central portion 31 and edge portion 32 of the tongue press, and the vertical strips 36 are also formed with a substantially uniform thickness. Thus, according to this invention, it is possible to provide the tongue press with a sufficient flexibility to well accommodate the differences in size and shape of the patient's tongue with no need of varying the thickness of the device at its respective portions as in the conventional tongue press devices.

Figure 3:
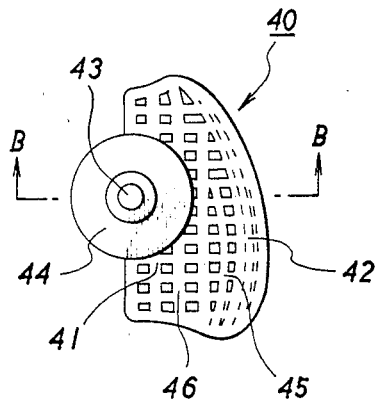
FIG. 3 is a top plan view of a half-covering type tongue press according to a second embodiment of this invention.
Figure 4:
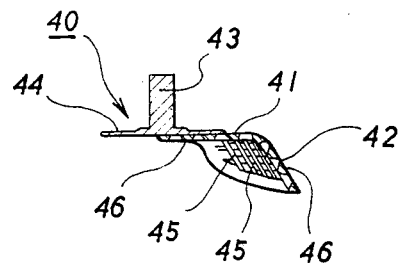
FIG. 4 is a sectional view taken along the line B—B of FIG. 3.

Referring now to FIG. 3, there is shown a top plan view of a half-covering type tongue press according to a second embodiment of this invention, and FIG. 4 is a sectional view taken along the line B—B of FIG. 3. In the drawings, numeral 40 designates generally the half-covering type tongue press, 41 the body portion thereof, and 42 the edge portion.

This half-covering type tongue press 40 is substantially equal to the one half of the above-described whole-covering tongue press 30 and designed to cover the half of the upper part and one side of the patient's tongue. The tongue press 40 also has a reticulate structure constituted by lateral strips 45 and vertical strips 46.

On the upper side of the body portion 41 of said tongue press 40 are provided a force-dispersing disc 44 for dispersing throughout the structure the force given to the tongue press 40 and a joining protuberance 43.

The edge portion 42 is formed integral with the body portion 41 and designed to cover and hold one side of the patient's tongue in position while protecting it from being injured by a dental instrument.

A pair of such half-covering tongue presses 40, one for covering the right half of the patient's tongue and the other for covering the left half, need to be prepared.

Figure 5:
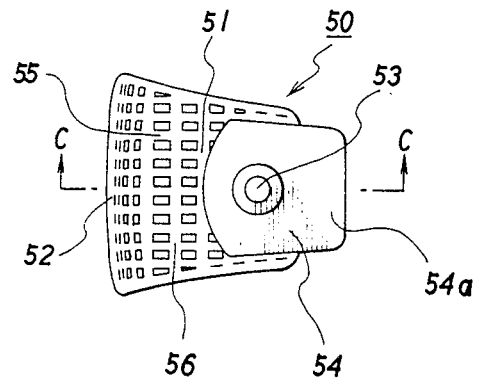
FIG. 5 is a top plan view of a partially covering type tongue press according to a third embodiment of this invention.
Figure 6:
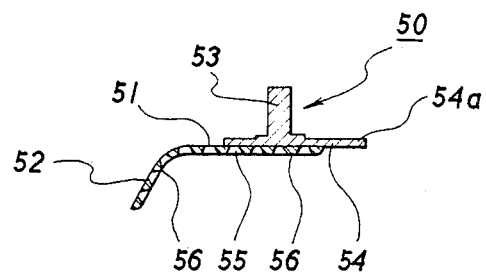
FIG. 6 is a sectional view taken along the line C—C of FIG. 5.

FIG. 5 illustrates a top plan view of a partially covering type tongue press according to a third embodiment of this invention, and FIG. 6 is a sectional view taken along the line C—C of FIG. 5. In the drawings, 50 designates generally the partially covering type tongue press, 51 the body portion thereof, and 52 the edge portion.

This partially covering tongue press 50 is designed to cover partially the upper part and one side of the patient's tongue. It is configured in conformity to the upper part and one side of the tongue and has a reticulate structure constituted by lateral strips 55 and verticals trips 56.

On the body portion 51 of said tongue press 50 are provided a rectangular force-dispersing and tongue-fixing fitment 54 and an erect joining protuberance 53.

Said fitment 54 is designed to dispers throughout the structure the pressing force applied to the tongue press 50, and one end 54a of said fitment 54 is placed on the teeth on the side opposite from the side of the tongue protected by the edge portion 52 so as to securely hold the tongue in position.

The edge portion 52 is formed integral with the body portion 51 and designed to cover and hold one side of the patient's tongue in position while protecting it from being injured by a treating instrument.

This partially covering type tongue press 50 can be used for either right side or left side of the tongue.

All of the described embodiments of tongue press according to this invention can be produced by properly molding, typically injection molding a natural or synthetic rubber material or a synthetic resin such as elastomeric resin which has both enough flexibility and heat and chemical resistance to remain unaffected by the treatment in an autoclave which is heated to around 130° C. or by various types of chemical disinfection.

Each tongue press according to this invention is not required to have different thicknesses at its body portion and edge portion, so that the mold used for producing such tongue press needn't be varied in clearance between the cope and drag and therefore the mold is obtainable at low cost.

The individual tongue presses may be tinted in different colors such as white, green, blue, yellow, etc., so that a tongue press with a particular color is used for a particular patient to ease his tension or malaise in application of the tongue press.

Any type of tongue press according to this invention, if prepared in pair only differing in size (one for adults and the other for children), can be applied to most of the patients.

Further, since the tongue press according to this invention has reticulate structure as described above, even if patient's saliva gets in between his tongue and the tongue in its use, such saliva readily flows out from the tongue press, so that the tongue press won't slip on the tongue but can securely hold the tongue in position. Also, the patient feels far less offensive in use of the present tongue press than in use of the conventional tongue presses.

The practical adaptation of the tongue press according to this invention to an external tongue press holder and an internal tongue press holder is explained below.

Figure 7:
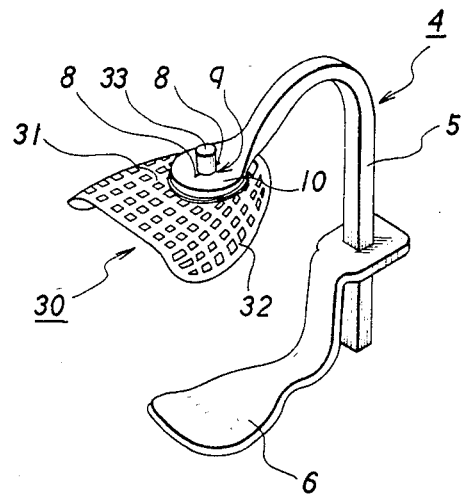
FIG. 7 is a perspective view of an external tongue press holder adapted with the whole-covering type tongue press according to this invention.
Figure 8:
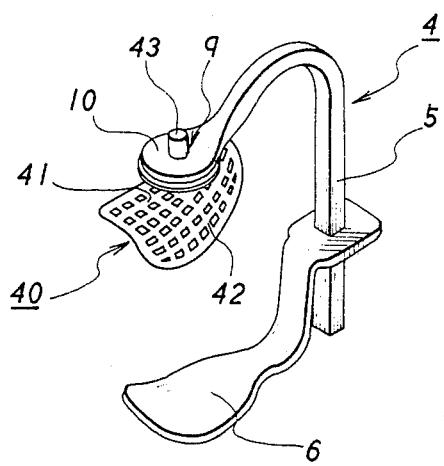
FIG. 8 is a perspective view of an external tongue press holder with the half-covering type tongue press according to this invention.

FIG. 7 is a perspective view of an external tongue press holder adapted with the whole-covering type tongue press according to this invention, and FIG. 8 is a perspective view of the external tongue press holder adapted with the half-covering tongue press according to this invention.

Any type of tongue press according to this invention can be detachably adapted to both external and internal tongue press holders as seen from FIGS. 7, 8, 10 and 11. That is, the whole-covering, half-covering and partially covering type tongue presses according to this invention can be selectively adapted to either external or internal tongue press holder according to the purpose of use.

Figure 13:
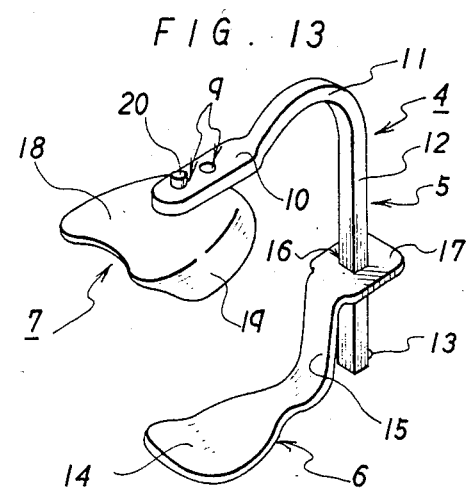
FIG. 13 is a perspective view of an external tongue press holder adapted with a conventional tongue press.
Figure 14:
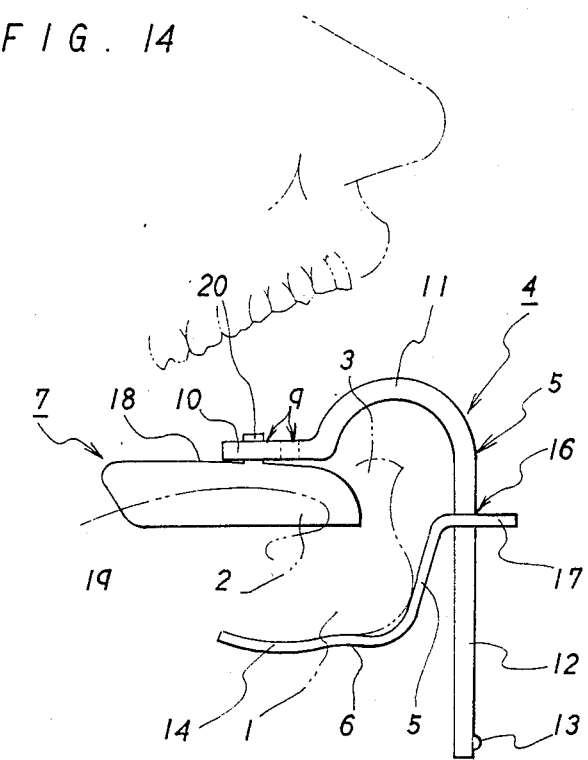
FIG. 14 is a diagrammatic side view of a patient's mandibular portion, showing the external tongue press holder of FIG. 13 as it was set in its use position.
Figure 15:
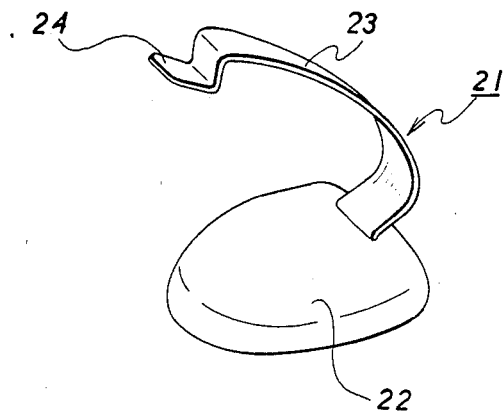
FIG. 15 is a perspective view of a conventional internal tongue press holder.
Figure 16:
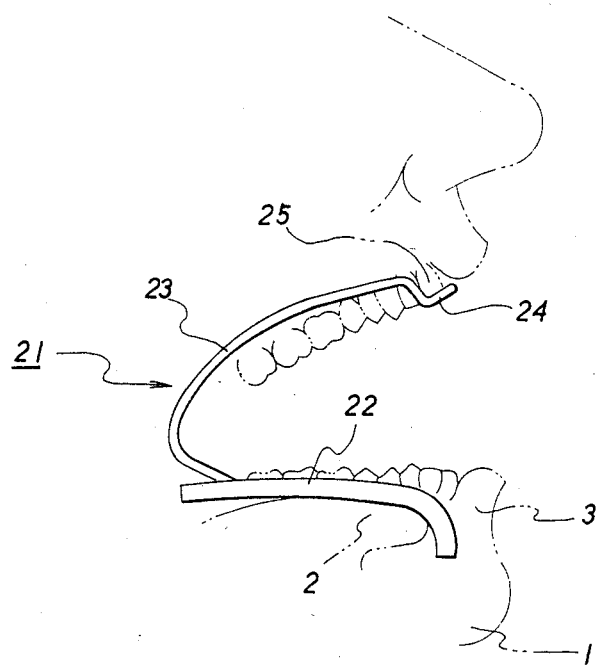
FIG. 16 is a diagrammatic side view of a patient's buccal portion for showing the internal tongue press holder of FIG. 15 set in its use position.
Figure 17:
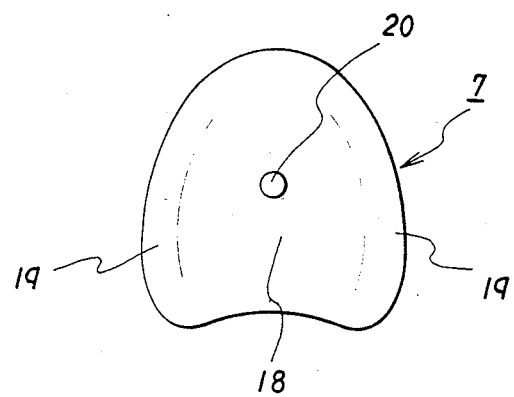
FIG. 17 is a top plan view of a conventional tongue press.
Figure 18:
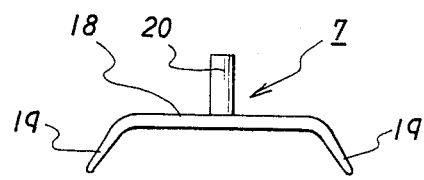
FIG. 18 is a sectional view taken along the line D—D of FIG. 17.

In case the whole-covering tongue press 30 according to this invention is adapted to an external tongue press holder 4 as illustrated in FIG. 7, the mode of use thereof is the same as described above in use of the conventional tongue press 4 with reference to FIGS. 13 and 14.

In this case, however, since the tongue press 30 is of a reticulate structure constituted by lateral strips 35 and vertical strips 36, it is possible to more securely hold the patient's tongue in position and to reduce the patient's uneasiness in application of the device.

In the tongue press holder shown in FIG. 7, cuts 8 may be provided in front and rear of the fitting hole 9 to afford a flexibility to the hole 9. In this case, it is desirable that the joining protuberance 33 on the tongue press 30 has a slightly greater size than the inner diameter of the hole 9.

Figure 9:
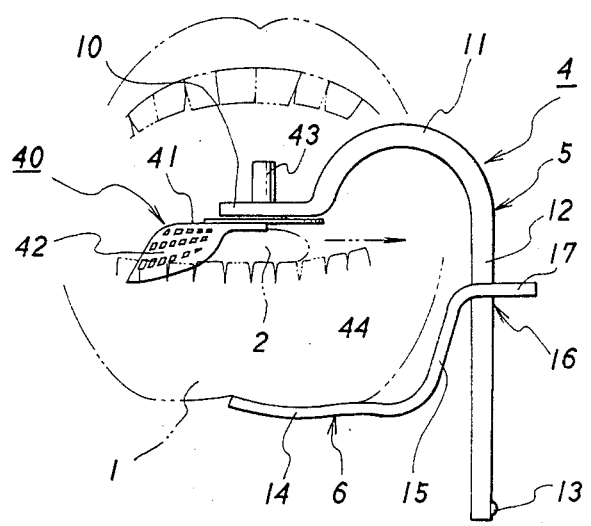
FIG. 9 is a diagrammatic frontal view of a patient's mouth where the external tongue press holder of FIG. 8 is set in its use position.

In use of the half-covering tongue press 40 adapted to an external tongue press holder 4 as illustrated in FIG. 8, said tongue press 40 is so placed as to cover one half of the patient's tongue 2, with the connecting member 5 and supporting member 6 being positioned on the opposite side from the half portion of the tongue 2 covered with said tongue press 40 as shown in FIG. 9.

In the dental treatments, it is rare that the treatment be conducted on the teeth on both sides of the alveolar ridge, and usually each treatment is conducted on a tooth on one side of the toothridge. In view of this, said tongue press 40 is designed to cover and protect one half and one side of the patient's tongue 2 for further bettering the feeling of the patient in application of the device. It is is to be also noted that the connecting member 5 and supporting member 6 are positioned on the opposite side from the half portion of the tongue 2 covered with said tongue press 40 so that the patient's tongue will be placed as much away from the location of tooth treatment as possible and that the tongue press holder 4 will not obstruct the treatment by the dentist. This holds true in use of the whole-covering type tongue press 30 adapted to an external tongue press holder.

Figure 10:
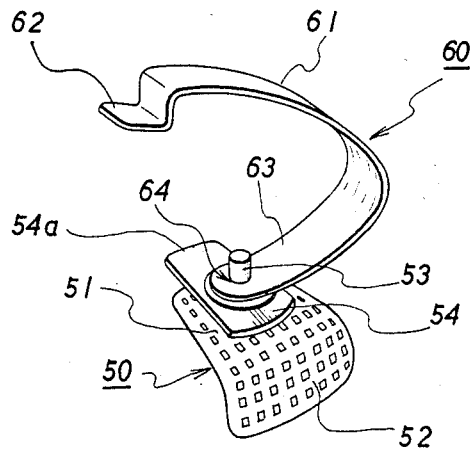
FIG. 10 is a perspective view of an internal tongue press holder adapted with the partially covering type tongue press according to this invention.
Figure 11:
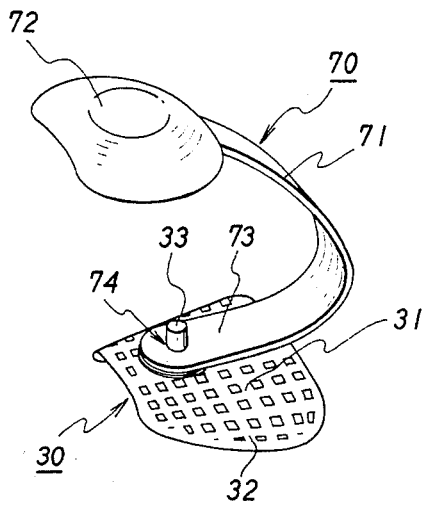
FIG. 11 is a perspective view of another internal tongue press holder adapted with the whole-covering type tongue press according to this invention.

FIG. 10 is a perspective view of an internal tongue press holder adapted with the partially covering type tongue press according to this invention, and FIG. 11 is a perspective view of another type of internal tongue press holder adapted with the whole-covering tongue press according to this invention.

The partially covering tongue press 50 according to this invention is designed to cover a part of the upper part and one side of the tongue with the body portion 51 and edge portion 52. An end 54a of the force-dispersing fitment 54 is placed on the teeth on the side opposite from the tongue portion covered with said tongue press 50, so that this device, even when adapted to an internal tongue press holder, can securely hold the tongue in position.

In this internal tongue press holder 60, a fitting hole 64 similar to that in the fixing portion 10 of the external tongue press holder 4 is provided in the fixing portion 63 at the lower end of the elastic curved portion 61 as illustrated in FIG. 10 to allow selective adaptation of any type of tongue press according to this invention.

Said hole 64 is smaller in diameter than the protuberance 53 on the tongue press 50. Cuts 8 may be provided in front and rear of the hole 64 as in the case of the hole 9 in said external tongue press holder 4 to afford a flexibility to the hole 64.

Abutment 62 is designed to abut against the upper front teeth of the patient in use of the tongue press holder 60 like in the conventional internal tongue press holder 21.

Beside the above-said type of internal tongue press which is set in engagement with the upper front teeth of the patient, there is also available a type which is set in abutment against the inside of the upper jaw of the patient to fix the tongue press in proper position.

This type of internal tongue press holder 70, as illustrated in FIG. 11, has a pad 72 at the upper end of the elastic curved portion 7, said pad 72 having a shape corresponding to the inside configuration of the palate, and a fitting hole 74 is provided in the fixing portion 73 at the lower end of said curved portion 71.

Figure 12:
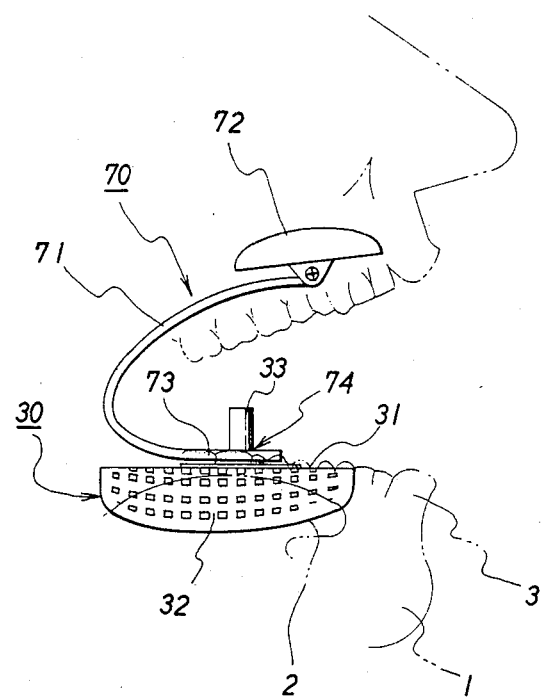
FIG. 12 is a diagrammatic side view of a patient's buccal portion for showing the internal tongue press holder of FIG. 11 set in its use position.

FIG. 12 is a diagrammatic side view of the mouth of the patient where the internal tongue press holder 70 of FIG. 11 is set in its use position.

In this internal tongue press holder 70, the top pad 72 is placed in abutment against the maxilla of the patient and the tongue press 30 is pressed down by the flexing force of the elastic curved portion 71 as shown in FIG. 12.

All types of tongue press according to this invention, that is, whole-covering type tongue press 30, half-covering type tongue press 40 and partially covering type tongue press 50, can be used in a suitable combination with any of the external and internal tongue press holders 4, 60 and 70, and also said tongue presses can be selectively adapted to any of said tongue press holders according to the purpose of use.

As described above, the tongue press according to this invention is capable of protecting the patient's tongue from being injured by a treating instrument such as high-speed cutting and polishing tools in a dental treatment, and also since the present tongue press has a reticulate structure constituted by lateral and vertical strips to provide a sufficient flexibility, the tongue press of one size cn be used for many patients differing in size and shape of the tongue.

Also, since the tongue press of this invention needn't be changed in thickness at its central body and edge portions, the cost for the mold used for producing the tongue press can be reduced and accordingly the tongue press can be offered at low price.

Further, even if saliva or other fluid gets in between the patient's tongue and the tongue press, such saliva or other fluid flows out of the tongue press because of its recticulate structure, so that the uneasiness of the patient in application of the device is alleviated and it also becomes possible to prevent the slip of the tongue and to securely hold the tongue in position.

Moreover, in case the treatment is conducted by stuffing sanitary cotton or the like between the tongue and the gun, such sanitary cotton won't slip out of the place even if it absorbs saliva or other fluid because the sanitary cotton is caught by the reticulate tongue press.

In addition, since all types (whole-covering type, half-covering type and partially covering type) of tongue press according to this invention can be used in free combination with either of external or internal tongue press holder, it is possible to select and use the optimal tongue press and its holder by considering the patient, substance of the treatment, etc.

What is claimed is:

1. A tongue press for use with an external or internal tongue press holder to restrain and protect a human tongue during dental treatment or the like, comprising a central body portion and an edge portion for covering at least a part of the upper surface and an edge of a tongue, said tongue press having a reticulate structure constituted by lateral strips and vertical strips and being uniform in thickness at both its central body portion and edge portion and a joining protuberance extending from the upper surface of said body for connection with a tongue press holder.

2. A whole-covering type tongue press according to claim 1 designed to cover the whole of the upper surface portion and both side portions of the tongue save its basal part and tip, said tongue pess having a configuration conforming substantially to the shape of the tongue and provided with a force-dispersing fitment between said joining protuberance and said body.

3. A half-covering type tongue press according to claim 1 designed to cover one half of the upper surface portion and one side portion of the tongue save its basal part and tip, said tongue press having a configuration conforming substantially to the shape of one half of the tongue and provided with a force-dispersing fitment between said joining protuberance and said body.

4. A partially covering type tongue press according to claim 1 designed to cover a part of the upper surface portion and a part of one side of the tongue, said tongue press having a configuration conforming substantially to the shape of the upper surface portion and one side of the tongue to be covered and provided with a force-dispersing fitment between said joining protuberance and said body, said fitment having a portion designed to be placed on the teeth on the opposite side of the mouth from said one side of the tongue.

5. A tongue press according to any of claims 1 to 4, wherein the lateral strips are greater in thickness than the vertical strips so that the lateral strips alone will contact the patient's tongue.

6. A tongue press for restraining a human tongue in a substantially flat position in the lower jaw and protecting the tongue during dental treatment or the like, comprising a body having a central portion and at least one edge portion and formed to cover a portion of the upper surface of the tongue from at least the longitudinal centerline of the tongue to an edge thereof, said body having a reticulate structure defined by longitudinally extending strips and laterally extending strips, the central and edge portions of said body being substantially uniform in thickness and a joining protuberance extending from the upper surface of said body for connection with a tongue press holder.

* * * * *

UNITED STATES PATENT AND TRADEMARK OFFICE
CERTIFICATE OF CORRECTION

PATENT NO. : 4,589,848

DATED : May 20, 1986

INVENTOR(S) : Miyako Inoue

It is certified that error appears in the above-identified patent and that said Letters Patent is hereby corrected as shown below:

```
Cover page, below "(22) Filed: Feb. 7, 1985" insert:
   --(30)  Foreign Application Priority Data
      Nov. 19, 1984 (JP)  Japan..........59-174343(U)--
```

Signed and Sealed this

Sixteenth Day of December, 1986

Attest:

DONALD J. QUIGG

*Attesting Officer*  *Commissioner of Patents and Trademarks*